United States Patent [19]
Paige

[11] Patent Number: 4,559,250
[45] Date of Patent: Dec. 17, 1985

[54] CONTAMINATION-CONTROL MATS

[76] Inventor: Raymond J. Paige, 61 The Point, Coronado, Calif. 92118

[21] Appl. No.: 591,678

[22] Filed: Mar. 21, 1984

[51] Int. Cl.$^4$ .............................................. A61F 13/02
[52] U.S. Cl. ..................................... 428/40; 428/345; 428/335; 427/40; 156/272.6; 156/306.3; 156/344; 15/215
[58] Field of Search ................. 428/345, 352, 40, 335; 427/40; 52/173 R; 156/272.6, 306.3, 344; 15/215

[56] References Cited

U.S. PATENT DOCUMENTS

| | | | |
|---|---|---|---|
| 3,501,797 | 3/1970 | Nappi | 428/40 |
| 3,785,102 | 1/1974 | Amos | 52/173 |
| 3,901,755 | 8/1975 | Martin et al. | 428/475.5 |
| 3,944,709 | 3/1976 | Levy | 427/40 |
| 4,421,780 | 12/1983 | Buzio et al. | 427/40 |

FOREIGN PATENT DOCUMENTS 1340636 12/1973 United Kingdom ................ 428/354

Primary Examiner—Edith Buffalow
Attorney, Agent, or Firm—Owen, Wickersham & Erickson

[57] ABSTRACT

A tacky mat stack employing sheets 0.4 mil to 2.5 mils thick of either high-density polyethylene or linear low-density polyethylene or low-density polyethylene, each sheet having been treated electronically on both sides, one side having about twice the dyne level of the other, and adhesive on the side having the higher dyne level. The adhesion pull load may vary from about ½ ounce to about 10 ounces per lineal inch.

10 Claims, No Drawings

CONTAMINATION-CONTROL MATS

This invention relates to improvements in contamination-control mats.

BACKGROUND OF THE INVENTION

Adhesive contamination-control mats of various sizes, configurations, materials, and constructions have been produced for many years. These products serve two primary functions: (1) To reduce contamination traceable to dirt carried by shoes and wheels by seizing the dirt and containing it on an adhesive surface; (2) to reduce the amount of shoe and heel carried dirt that might be converted into atmospheric dust (micro-particulate matter) if not stopped and contained on the adhesive surface. Reduction of dirt on shoes, wheels, and in the air results in the reduction of potentially dangerous bacteria and thus may serve to reduce infections in patients in surgical operating rooms and other critical patient care areas. Reduction of such dust also reduces failure of electronic parts and improves laboratory processes where dust contamination control is vital.

The incidence of hospital bacterial contamination has been one of increasing frequency and fact. The growing number of areas called Clean Rooms installed by laboratories and industry to help control atmospheric microparticulate contamination is well recognized and has created a new phase of laboratory design over the past twenty years. At this writing, annual sales of adhesive-coated contamination-control mats exceeds $20,000,000.00 The various early designs of such adhesive mats have evolved down to two basic product constructions: a thick, approximately one-quarter inch thick single-layer mat made of a soft polyvinyl chloride material and a multi-layer, stack of adhesive-coated plastic films.

Single-layer mats have the advantage that the weight and inertia of the mat enables it to lie flat on the floor surface without any specific added means of floor adhesion. Also, the surface has a very low level of adhesiveness, yet its soft upper-facing surface does tend to remove dust and dirt from shoes and wheels crossing across its surface. The product, therefore, has the advantage of being both effective and comfortable to walk upon and to stand upon. Its adhesive level is not apparent to the user; it does not pull on the shoe. However, when the surface becomes dirtied, it quickly becomes ineffective. Then the dirt must be removed by a water washing process and the surface dried with a lint-free towel before the product is again ready for use. Over a period of many such washings, the surface becomes scratched and pitted and as a result loses much of its effectiveness, because of the continual wearing process. Another negative factor is that the product has a high profile due to is thickness of approximately one-quarter inch, thus creating a trip hazard. Mainly because of high initial cost to the buyer, the gradual loss of function, and the high labor cost of continual constant rewashing, the market penetration of the simple-layer mat has been limited.

Multi-layer mats, comprise a stack or lamination of, presently, up to about thirty layers of pressure-sensitive adhesive-coated plastic films with the adhesive coat facing upward. The adhesive surface removes dirt and dust from shoes and wheels. When its surface is dirty, and therefore loses its effectiveness, the top sheet is removed from the stack and discarded, revealing another clean sticky surface, ready for use. No washing is required or attempted; so no degradation of surface of the type encountered by single-layer mats occurs, for there is no long term wear since each sheet is removed and discarded when dirty. Hence, this construction has attained the major market share. However, it has a high cost of daily usage. The two major producers of the stack concept product use an adhesiveness level which is very high as compared to the single layer product previously described, and as a result these products are uncomfortable to stand upon. Shoes get stuck and have sometimes been pulled off. The user therefore tends to walk across the surface as quickly as he can, if it is not possible to avoid walking over the mat. The highly aggressive tack level and the high cost of usage generally restricts the product to small entrance areas only.

These prior-art laminated stacks have been constructed of adhesive-coated low-density polyethylene films, each layer being approximately 2.5 mils in thickness or greater, plus an upward facing pressure-sensitive adhesive layer of approximately 0.333 mils. The product of one major producer, a thirty layer stack, is about ninety-four mils thick. The stack is held to the floor by means of a pressure-sensitive adhesive coating on the downward facing bottom layer. The thickness of these products creates a problem of edge height resulting in possible tripping of the user or scuffing of the product's edges. One producer helps to solve this height problem by mechanically bevelling the edge. The other producer does not bevel the edge but instead emphasizes the edge by placing the product in a rigid frame which is secured to the floor.

A major problem with current multi-layer stacks is the danger of premature sheet-to-sheet delamination. A clean rubber-soled shoe, typical of those used in hospitals, worn by a person weighing 150 pounds and pressed to an adhesive surface of ten ounces of adhesion (method 2050 or FTM STD NO-101 B) will develop 320 ounces of direct upward pull. This upward pull tends to pull the sheet loose from the underlying layer and to wrap around the shoe or wheel, thereby resulting in potential danger to the user. One company helps to solve this problem by providing a tiny dry-stripe non-adhesive coated edge on the edges of each sheet. Therefore a clean shoe sole does not come into contact with adhesive at the edge of the adhesive-coated sheet or layer where the danger of delamination is greatest. The other major producer uses its floor frame to good advantage. The edge of the frame being higher than the edge of the floor mat, the shoe of the user cannot come into contact with the extreme edge and, thereby, helps prevent delamination.

Current adhesive-coated contamination control plastic film mats are constructed of low-density polyethylene film at least 2.5 mils thick. The tensile strength of uncoated low-density polyethylene is generally 2800 p.s.i. Low-density polyethylene film can be made more resilient or stretchy by the addition of small percentages of other chemicals such as polyvinyl chloride. When such a sheet of plastic film is adhered to an adhesive-coated film which has an adhesion of eight to ten ounces of pull or adhesion per inch of width, the film must be strong enough to withstand the pull load of removal without tearing or shredding. This requisite strength has heretofore been accomplished via film thickness. A one-mil low-density polyethylene film would often tear upon removal from a ten-ounce adhesive-coated substrate.

With both concepts of the tacky mat product, the multi-layer stack and the washable single-sheet, the dirt and bacteria remain adhered to the sticky surface until either peeled off (as with the stack product) or washed (as with the single-layer washable product). One producer has incorporated an anti-bacterial chemical into its adhesive which, it claims, helps to kill the bacteria while they are held in place on the contamination control mat.

OBJECTS OF THE INVENTION

One object of this invention is to provide a tacky mat which will give the user at least a fifty percent greater cost efficiency than is given by currently available tacking mats, while also giving equal dirt-removing capability.

Another object is to provide a tacky mat with an optional low-tack, comfortable-to-use adhesive surface so that larger areas of floor may be covered without objections from the users.

Another object is to provide a stack of pressure-sensitive adhesive coated films whose individual sheet thickness may be about one-half the thickness of current pressure-sensitive adhesive-coated films used in stack pads. Corollary objects are to enable stacks containing more sheets, to enable less frequent stack changes, or, alternatively, to enable thinner stacks have the same number of sheets.

Another object is to provide a strong sheet-to-sheet lamination so as to prevent premature delamination.

SUMMARY OF THE INVENTION

This invention comprises a tacky mat stack, preferably employing sheets 0.4 mil to 2.5 mils thick of either high-density polyethylene or linear low-density polyethylene or (non-linear) low-density polyethylene each sheet having been treated electronically on both sides, one side having about twice the dyne level of the other, and adhesive coated on the side having the higher dyne level. Thicker sheets can be used with some loss in advantage. The adhesive itself has a tack value or adhesive pull load of from about one-half ounce up to about ten ounces per linear inch.

DESCRIPTION OF SOME PREFERRED EMBODIMENTS OF THE INVENTION

The invention embodied herein can use a film as thin as 0.4 mil to 2.0 mils thick, with a one-mil film being the nominal choice. Thicker films can be used but are less advantageous. Thinness of film is desirable for two very important reasons: (1) with the use of a one-mil film, for example, a stack of one hundred layers would have a total height of one hundred mils, whereas with the commonly used nominal three-mil film, including adhesive, a stack of one hundred layers would have a height of three hundred mils. Since a three-hundred mil height would be a significant safety hazard, the manufacturers have limited themselves to a thirty-layer stack. A 100-layer stack would otherwise, however, have a major advantage to the user, since each installation of a replacement stack to the floor is burdensome and time consuming. (2) The other major advantage of thin plastic film is low cost. Plastic films are normally priced by the pound. At today's writing commonly used low-density polyethylene film costs the floor pad manufacturer about eighty cents per pound. A one-mil film yields three times as much working-surface area of film per pound as a three mil film. To illustrate further, a three-mil low-density film yields 78 square feet of surface area per pound while the same material in a one-mil thickness yields 208 square feet of surface area per pound.

To enable the use of a one-mil film, this invention preferably employs strong, high density polyethylene or, as an alternative, linear low-density polyethylene.

High-density polyethylene has a typical film tensile strength of 4800 PSI, ASTM test method D882. This is sufficient to withstand an adhesive pull load from an underlying layer of ten ounces pull per lineal inch of width. Linear low-density film also has a tensile strength sufficient to withstand ten ounces of adhesion per inch of width without tearing, typically 6000 p.s.i. Low density polyethylene in comparison has a typical tensile strength of 2800 p.s.i.

Films thinner than one mil can be used in a stack of this invention, so long as the adhesive pull load is reduced. This invention includes the use of 0.4 mil high density or linear low-density film with adhesive pull loads of five ounces or less per lineal inch.

As discussed previously, the relatively thick low-density polyethylene films commonly used provide a nominal ninety-mil height in a stack thirty layers high. To prevent edge delamination and sheet-to-sheet delamination, and tripping, it has been noted that one manufacturer employs a highly visible floor frame with an inside edge higher than the stack of adhesive coated films placed therein. The other producer uses beveled edges on its mat and incorporates a narrow dry stripe on the upper edge surface of each layer. Both of these techniques were described above.

In contrast, the present invention comprises a stack of adhesive-coated films which does not require either a frame or a beveled edge, and results in ultimate cost savings through the reduction in manufacturing labor on one hand and the elimination of the floor frame on the other.

To cause adhesive to adhere strongly to the surface of a polyethylene film, it is necessary to distress the ordinarily smooth surface of the film. This treatment of the film surface is accomplished by a a high electronic discharge onto the surface and is commonly called a corona treatment. Without this corona treatment the adhesive would tend to rub off from the plastic film or to stick to a clean rubber sole shoe or cart wheel and transfer thereto. This electronic or corona treatment of film is well known and is widely used in adhesive coating operations. However, the film of the products currently in the market place are not similarly treated on the back-side of each sheet, in order to enable the sheets to separate easily one from the other. Easy separation is an advantage when the user is removing a dirty sheet, but it is a hazard when it occurs prematurely and results in sheet-slippage during use.

In the present invention, the sheets are held tightly together and prevented from premature delamination by electronic treatment of the non-adhesive side of the individual sheets. When the uncoated side of the plastic sheet is given electronic or corona treatment, the non-adhesive coated surface adheres more strongly to the underlying, upper-facing adhesive-coated sheet.

The corona electronic treatment level produces a force and so can be measured in dynes. Thus, a ten-dyne treatment is less disruptive to the surface of a plastic film than is treatment at a forty-dyne level. Adhesive which is coated onto a plastic film with a forty-dyne treatment level binds tightly to the corona treated surface of the film. Adhesive coated onto a plastic film with a ten-dyne or twenty-dyne treatment level is bound less tightly than the adhesive applied to a forty-dyne treated surface. This differential of adhesive adherence to film is a key feature of the invention.

When adhesive is coated onto a plastic film at a forty-dyne treatment level and subsequently this adhesive-coated film is laminated to a plastic film which also had been treated at the forty-dyne level, the adhesive adheres just as tightly to the new surface as to the plastic film surface onto which it had been originally coated. In that case, the two films do not separate without tearing or without some delamination of adhesive from one of the two forty-dyne surfaces. If an identical adhesive-coated film is laminated to a plastic film surface which had no corona treatment, the films are later separated easily with no tearing and no adhesive transfer. At ten dynes, the two films are somewhat harder to separate, and at twenty dynes are harder still, but the adhesive still stays well adhered to its original surface.

According to the present invention, adhesive-coated films can be held together in stack form and still be properly released from each other, by controlled usage of corona electronic discharge.

The typical adhesive coated surface of the two largest producers of contamination control mats (approximately 90% of the total market) uses adhesive to provide a ten-ounce pull load per lineal inch. This can be measured by adhering an adhesive-coated film one inch wide to a clean #4 polished sheet of stainless steel. This strip of film is then removed via a pulling device which measures the amount of pull in ounces required to remove it from the stainless steel at a pull rate of twelve lineal inches per minute (method 2050 of FTM STD NO-101 B).

In contamination-control mat usage this nominal ten-ounce adhesive surface faces upward and is walked upon. A clean, smooth, rubber-soled shoe would contain a nominal surface area of thirty two square inches. If this shoe was pressed upon the contamination-control mat surface and pulled directly upward, a force of 320 ounces of up-pull would be exerted on the pad surface; therefore the sheets of the mat must be tightly bonded to each other in order to prevent premature delamination, which is particularly critical at the extreme edges of the mat.

According to this invention, the use of an electronic treatment is applied to both sides of the film, with the uncoated side of the film receiving the treatment at a level of about half of the electronic treatment level given to the adhesive-coated surface. This relationship provides the tight bonding requisite to hold the stack together while still resulting in the sheets releasing from each other when required to do so. Thus, if the adhesive-coated side of the sheet is treated at a 42 dyne level, the backside should be similarly treated but at a level of about 21 dynes. Optimum results for different films or film surfaces adhesions may vary, and the ratio may vary up or down from about the fifty percent level. The adhesive-coated side is preferably treated at a level of about 40 to 50 dynes and the non-coated side is preferably treated at a level of about 10 to 30 dynes.

Thus, this invention employs electronic corona treatment on both sides to help prevent premature sheet-to-sheet delamination and to eliminate the need for either edge bevelling or floor frames.

As stated above, an adhesive coated surface with an adhesion level of ten ounces per lineal inch produces a nominal up-pull of about 320 ounces when stepped upon with a clean rubber-soled shoe. A tacky mat stack of this invention, employing electronic treatment on the uncoated side of the plastic sheet in the indicated amount will not delaminate any one sheet from another sheet.

The invention thus includes the use of a stack of thin films 0.4 to 2.5 mils thick with electronic or corona treatment on both faces, the uncoated face having no more than about half of the level of treatment of the adhesive coated face. Relatively high levels of upward-facing adhesion, in the range of ten ounces per lineal inch, may be employed, but lower adhesion values, down to about ½ ounce per lineal inch, may be used depending upon user preference.

Because of the undesirable results obtained with the commonly used high-tack adhesives, prior-art tacky mat stacks have generally been limited to covering small floor areas. Single-layer mats as described above, have often been used to cover large floor areas because their adhesiveness is very low, being in the range of one-half ounce pull on a new pad versus the ten-ounce pull for the stack-type mat. Tests have shown that dirt will be transferred to even a very low tack adhesive when the dirt is pressed down onto the surface, under the weight of a human being or cart. Further tests have shown that once an adhesive surface is dirtied, it no longer serves to remove dirt. Some users of dirt-removing floor mats recognize that a highly aggressive adhesive surface does not necessarily mean more efficiency in dirt removal.

Dirt and dust are picked up by an essentially non-adhesive rubber soled shoe or rubber cart wheel during normal walking or rolling, because the rubber wheel or shoe sole is more attractive (i.e., adhesive) to the particulate matter than is the hard surfaced floor on which the dirt had been sitting. When the same dirtied shoe or wheel crosses a surface that is more adhesive than itself, the dirt transfers to the more adhesive surface. Thus a relatively low level of adhesion is all that is needed to be more attractive to dirt than its original shoe or wheel cart. However, once the more adhesive surface is dirtied, it is no longer capable of removing particulate matter from a shoe or cart wheel.

Therefore a low level of adhesion is not necessarily less efficient in dirt removal than a highly adhesive surface. Many contamination control users prefer a low tack, comfortable mat surface but dislike the washing process, because of slip danger and the labor cost. This invention thus preferably uses low-adhesion adhesives in a stack product configuration with an adhesive pull load range as low as one-half ounce per lineal inch. This gives the user the benefit of a surface that is comfortable to walk upon and enables use of large surfaces areas along with easy disposability, while eliminating the necessity of washing.

The invention also employs aggressive adhesives, when desired by the user, up to an adhesion pull range of ten or more ounces per lineal inch.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A tacky mat stack employing a stacked series of sheets of either high-density polyethylene or linear low-density polyethylene or non-linear low density polyethylene each sheet having been treated electronically on both sides, and adhesive coated on its upper side, said upper side having about twice the dyne level of electronic treatment of the lower, non-adhesive coated side, to provide preferential action that enables trouble-free sheet separation during removal of each uppermost sheet from said stack while also avoiding loss of the adhesive coating from the sheets below and preventing premature delamination of said stack.

2. The stack of claim 1 wherein the adhesive has an adhesion pull of from about one-half ounce to about ten ounces per lineal inch.

3. The stack of claim 1 wherein the electronic treatment on the adhesive side is about 40 to 50 dynes and that on the non-adhesive side is about 10 to 30 dynes.

4. The stack of claim 1 wherein the sheets are from about 0.4 mil to about 2.5 mils thick.

5. A tacky mat stack employing a stacked series of sheets 0.4 mil to 2.5 mils thick of high-density polyethylene, each sheet having been treated electronically on both sides, the upper side of each sheet being adhesive coated and having about twice the dyne level of electronic treatment of the lower side, which has no adhering to provide preferential action that enables trouble-free sheet separation during removal of an upper sheet from said stack while also avoiding loss of the adhesive coating on the sheets therebelow and preventing premature delamination of said stack.

6. The stack of claim 5 wherein the adhesive has a pull load of about ½ to about 10 ounces.

7. A tacky mat stack employing a stacked series of sheets, each 0.4 mil to 2.5 mils thick, of linear low-density polyethylene, each sheet having been treated electronically on both sides and having adhesive applied to the upper side only, the upper adhesive coated side having about twice the dyne level of electronic treatment of the lower side, to provide preferential action that enables trouble-free sheet separation during removal of an upper sheet from the stack while also avoiding loss of the adhesive coating on the sheet therebelow and preventing premature delamination of said stack.

8. The stack of claim 7 wherein the adhesive has an adhesion pull of from about one-half ounce to about ten ounces per lineal inch.

9. A tacky mat stack employing a stacked series of sheets 0.4 mil to 2.5 mils thick of non-linear low-density polyethylene, each sheet having been treated electronically on both sides and having tacky adhesive applied only to its upper side, the upper, adhesive coated side having about twice the dyne level of electronic treatment of the lower side to provide preferential action that enables trouble-free sheet separation during removal of an upper sheet from the stack while also avoiding loss of the adhesive coating on the sheet therebelow and preventing premature delamination of said stack.

10. The stack of claim 9 wherein the adhesive has an adhesion pull of from about one-half ounce to about ten ounces per lineal inch.

* * * * *